United States Patent [19]

Drury et al.

[11] Patent Number: 4,516,522

[45] Date of Patent: May 14, 1985

[54] SLIDE PREPARATION APPARATUS

[75] Inventors: F. Robert Drury, Lexington; Marshall D. Graham, Framingham, both of Mass.

[73] Assignee: Coulter Electronics, Inc., Hialeah, Fla.

[21] Appl. No.: 434,378

[22] Filed: Oct. 14, 1982

[51] Int. Cl.³ .................... B05C 17/10; B05C 11/04; B05C 13/02
[52] U.S. Cl. .................................. 118/120; 118/100; 118/108; 118/207; 118/413; 118/500; 15/104 S
[58] Field of Search ............... 118/100, 120, 206, 207, 118/401, 500, 413, 415, 108; 427/2; 206/456; 15/104 S

[56] References Cited

U.S. PATENT DOCUMENTS 3,470,847 10/1969 Chapin et al. ................. 118/100
4,392,450 7/1983 Prevo ............................ 118/120

Primary Examiner—Norman Morgenstern
Assistant Examiner—Robert J. Steinberger, Jr.
Attorney, Agent, or Firm—Silverman, Cass & Singer, Ltd.

[57] ABSTRACT

A portable, manually operable device for preparing a monolayer film of a biological fluid sample or the like on a slide for microscopic examination. Said device includes a base for retaining the slide thereon and a spreader manually movable linearly relative to the base and slide in a pass which spreads a sample of the fluid on the slide into such a monolayer. Preferably, the spreader is constructed to be disposable.

7 Claims, 6 Drawing Figures

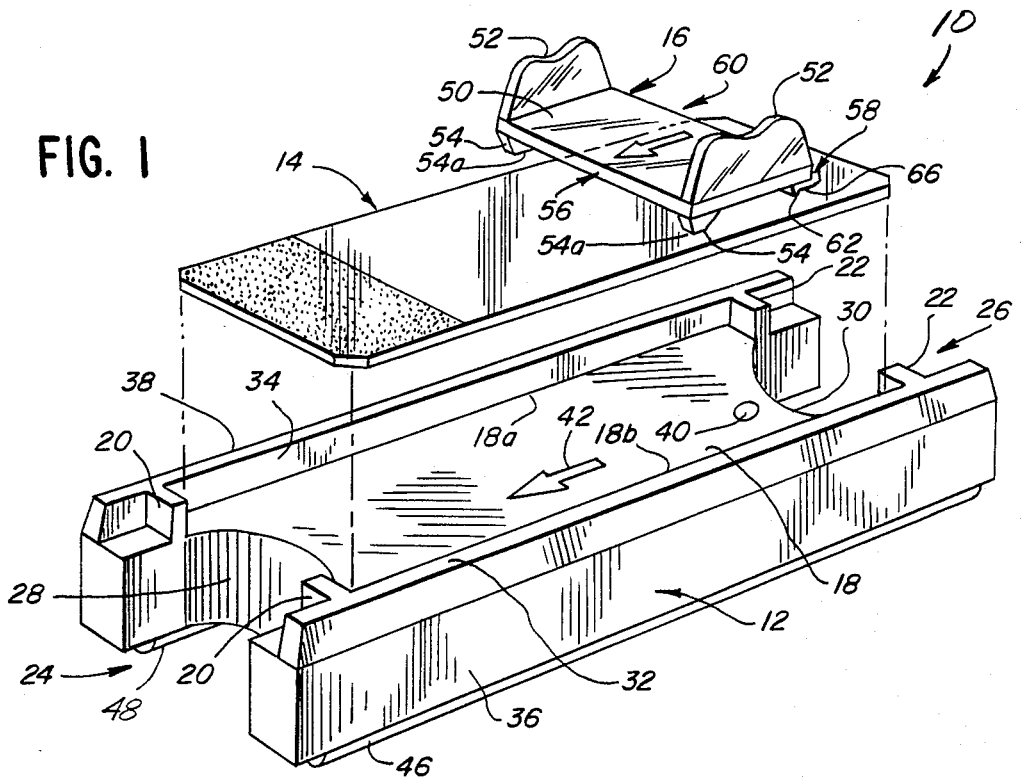

FIG. 4
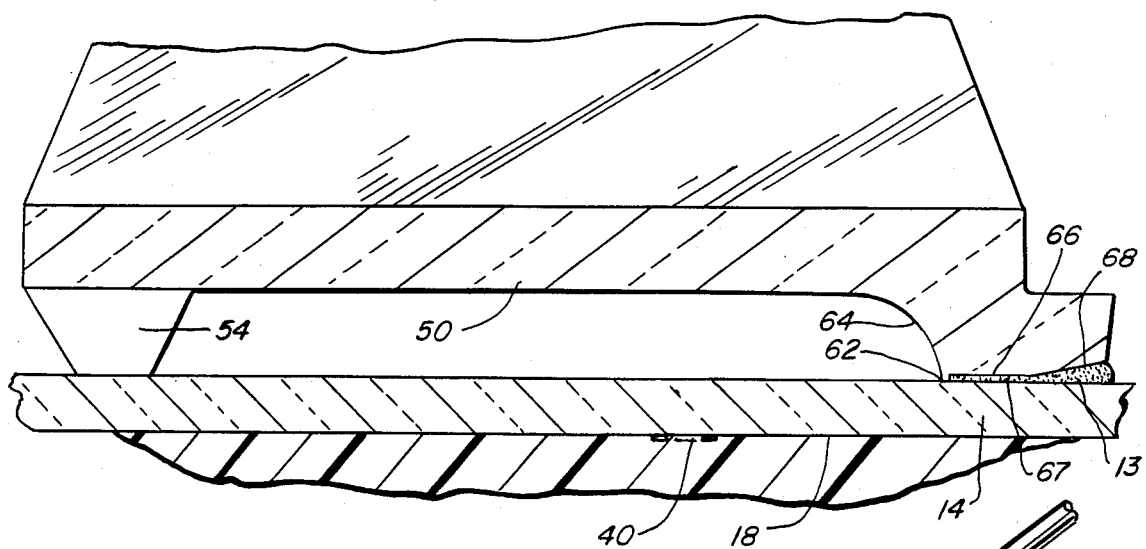
FIG. 5
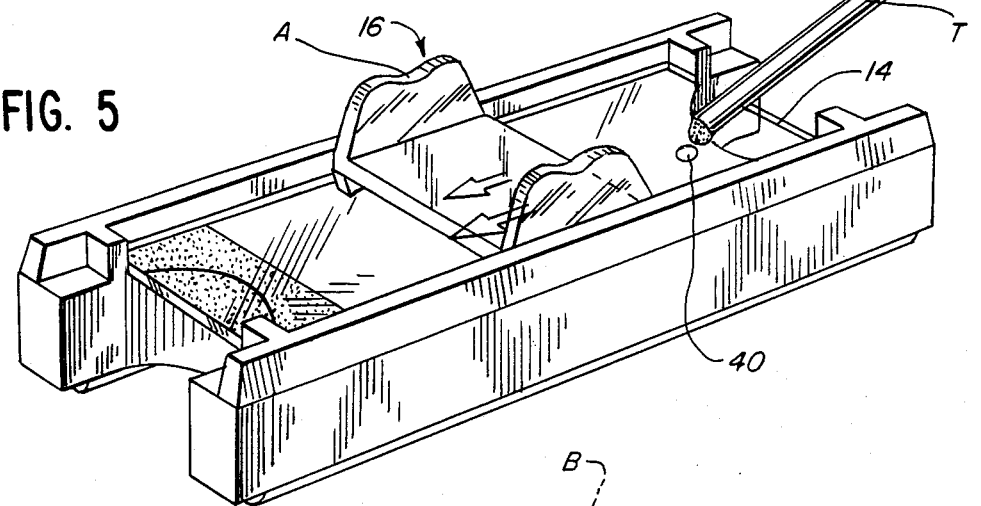
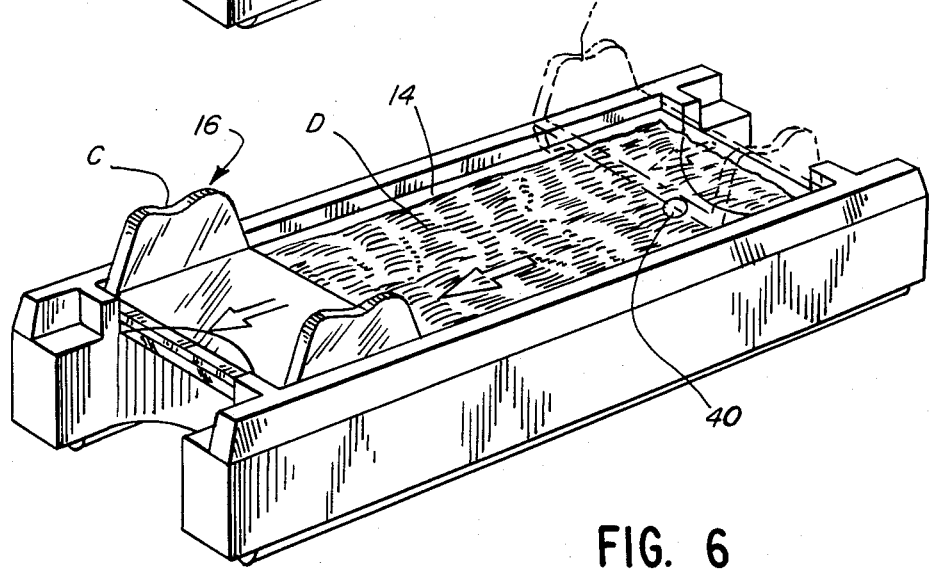
FIG. 6

SLIDE PREPARATION APPARATUS

BACKGROUND OF THE INVENTION

This invention generally relates to apparatus for the preparation of a fluid sample upon a slide for microscopic analysis, and more particularly, to improved apparatus for supporting the slide and spreading the sample thereon.

Prior art devices have employed a base on which a slide to be stained is supported flat on a support surface thereof. A spreader is manually movable linearly relative to the base and engaging the surface of the slide with appreciable downward force so that the fluid sample can be spread over the slide to form a so-called "monolayer" of the sample. The spreader is intended to be disposable after each use thereof. Typically, a blood sample is spread into a monocellular layer on the slide which can then be microscopically examined for blood cell differential screening.

Several dificiencies exist in such prior art devices. As structured, the spreader frictionally engaged said support surface so that it formed grooves or ruts in the support surface of the base after multitudinous passes. Eventually irregularities in the path of the movement of the spreader relative to the slide actually interfered with uniformity of spreading of the sample and thereby prevented achieving the desired monocellular layer consistently with the same base which was not intended to be disposable. Also, the base tended to deform or flex downwardly because of the necessity to press downwardly on the spreader when making the monolayer. This deformation or flexing contributed to breakage of the slides on occassion as well as possible non-uniformity in monolayer spread of the sample on the slide.

SUMMARY OF THE INVENTION

In accordance with this invention, apparatus is provided for preparing a monolayer of a biological fluid sample, such as blood, on a slide in which the support surface of the base for supporting the slide enables the sample spreader member to ride entirely upon the slide in the linear movement of said spreader over the slide by providing a pair of guide rails upstanding along opposite side edges of the support surface. The spreader is dimensioned to be positioned between the guide rails which maintain the alignment of the spreader upon the slide during its linear movement and not engaging the support surface. Firm downward pressure on the spreader during such linear movement is permitted without forming grooves or ruts in the support surface.

Further, the base is provided with rigidifying means which prevent flexing or deformation of the support surface under the downward pressure exerted upon the spreader during its linear movement over the slide. In addition, the spreader can be provided with tapered legs to reduce the frictional area of engagement with the slide in order to facilitate proper movement of the spreader upon the slide when preparing the monolayer.

BRIEF DESCRIPTION OF THE DRAWINGS

FIG. 1 is an exploded, perspective view of a slide preparation device embodying this invention;

FIG. 2 is a side elevational view of said apparatus assembled for operation with portions broken away to show details and illustrating diagrammatically, in part, three positions of the spreader riding on the slide in the preparation of the monolayer film thereon;

FIG. 3 is a sectional view taken along lines 3—3 of FIG. 2 and in the direction indicated generally;

FIG. 4 is a fragmentary view taken on FIG. 2 and enlarged to illustrate a broken outline position of the spreader at the right side end of FIG. 2 and with a fluid sample located for being spread when the spreader is moved to the left in FIG. 2;

FIG. 5 is a perspective view of said apparatus illustrating initial deposit of the fluid sample upon the slide;

FIG. 6 is a perspective view illustrating the position of the spreader after the monolayer film has been formed on the slide.

DESCRIPTION OF THE PREFERRED EMBODIMENT

Referring to FIG. 1, the slide preparation device embodying the invention designated generally by reference character 10. Apparatus 10 includes a base 12 for supporting a typical laboratory slide 14 upon which a monolayer film of biological fluid is to be formed for microscopic analysis. One specialized use of apparatus 10 contemplates a sample of blood 13 being spread manually upon slide 14 by a spreader 16 in a linear movement so as to distribute the blood in a monolayer or monocellular film upon the slide 14, as more fully described hereinafter.

Base 12 is fabricated preferably from a rigid and tough, but easily molded material, for example acrylonitrile-butadiene-styrene resin (ABS). Base 12 is a generally rectangular structure having a horizontal, upper surface 18 which forms a bed upon which slide 14 is supported. The slide is placed between a pair of positioning posts 20 and 22 located adjacent respective ends 24 and 26 of the base 12. Each end 24 and 26 is provided with a respective inwardly facing indentation 28 and 30 between a respective pair of positioning posts 20 and 22 so as to provide clearance space for gripping the slide 14 to facilitate its placement on and removal from surface 18.

Base 12 has a pair of elongate side rails 32 and 34 which are integral with and upstanding from respective edges 18a and 18b of surface 18 positioned above respective opposing sides 36 and 38 of the base 12. Each side rail 32 and 34 extends generally the entire length of the base between a respective one of each pair of positioning posts 20 and 22. Side rails 32 and 34 upstand from the sides of the slide 14 when the slide is positioned between posts 20 and 22 for preparation of the fluid film. In addition, rails 32 and 34 function as guides during linear movement of the spreader 16.

Referring to FIG. 1, surface 18 is provided preferably with an indicator 40 located generally equidistant between rails 32 and 34 and adjacent one of the indentations 30. The indicator 40 designates the location for deposit thereon of the blood sample 13 upon the slide 14, as illustrated in FIG. 5. Surface 18 also can be provided with a directional arrow 42.

As illustrated in FIG. 3, base 12 is provided with rigidifying means for the surface 18. Illustrative of such means is a plurality of elongate rib members 44 depending from surface 18. Ribs 44 are spaced apart and are parallel along the length of and between the ends 24 and 26 of the base 12. Preferably, ribs 44 extend the entire length of base 12 in order to assure rigidity sufficient to prevent flexing or deformation of surface 18 when substantial downward force is exerted manually on the spreader 16 during smear preparation. Such rigidity of the base is desired in order to provide proper support of the slide 14 which will prevent its breaking or cracking experienced with previous slide bases lacking such structural rigidifying means. While sufficient rigidity of the base could be provided by molding the region below surface 18 in solid or with a single, wide rib, the multiple rib structure substantially reduces the resin consumption and cooling time of the molding cycle.

Additionally, base 12 can be provided with a pair of feet members 46 and 48 located generally below respective sides 36 and 38. As illustrated in FIG. 1, feet 46 and 48 preferably extend the entire length of base 12. Feet 46 and 48 function to maintain base 12 stationary on the work surface (not shown) during the slide preparation. Preferably, feet 46 and 48 are fabricated from a somewhat resilient material, for example a silicone elastomer, which will resist displacement of the base 12 during the spreader movement. As illustrated in FIG. 3, feet 46 and 48 have a "T" configuration including a respective tongue formation 46a and 48a engaged between a respective side 36 and adjacent rib 44a, and side 38 and adjacent rib 44b.

Spreader 16 preferably is fabricated by injection molding, for example, from crystal grade polystyrene which enables the spreader to be inexpensive and transparent. As best illustrated in FIGS. 1, 3 and 4, spreader 16 includes a horizontal, planar platform 50 of generally rectangular configuration. The spreader has a pair of gripping members 52 upstanding from opposing sides of platform 50. A pair of leg members 54 depend from the opposite sides adjacent the front end 56 of the platform 50. The bottom end 54a of each leg 54 is tapered to reduce the area frictional engagement with slide 14 for supporting said front end 56 on slide 14, as best shown in FIG. 3. Spreader 16 has a blade member 58 which depends from the platform 50 adjacent to the rear end 60. Blade 58 extends parallel to said rear end 60 and includes a narrow, flat edge 62 forming the bottom edge of the blade 58 which engages the slide 14. In the preparation of a smear, the legs 54 and blade 58 ride entirely on the slide 14, as best shown in FIGS. 2 and 4. Accordingly, the entire linear movement of spreader 16 across the slide 14 does not produce grooving in the support surface 18 of base 12.

Blade 58 includes an arcuate formation 64 which joins the bottom edge 62 and the platform 50. Blade 58 is provided with a planar, recessed surface 66 which extends generally parallel to the platform 50 from the bottom edge 62 in the direction generally opposite to the front end 56. The recessed surface 66 provides a clearance space 67 between the blade member 58 and the slide 14 for the formation of a thin film or monolayer of the sample fluid as described hereinafter. The recessed surface 66 intersects a rearwardly inclined surface 68 which forms an angle of approximately 15° above the horizontal recessed surface 66.

Referring to FIGS. 2 and 5. To use apparatus 10, a clean slide 14 first is placed on the bed surface 18 of the base 12 between the four positioning posts 20 and 22 so that the unfrosted end of the slide is positioned over the indicator 40. A spreader 16 is placed onto the center of the slide between the guide rails 32, 34 so that blade 58 faces, but is spaced from, the indicator 40, as illustrated in the middle position A of the spreader 16 in FIG. 2. A blood sample 13 of approximately 5 to 6 microliters is then deposited on the slide over the indicator 40 using a capillary tube T, as illustrated in FIG. 5. The spreader 16 is moved manually through the blood deposit with a substantial downward force on handles 52 until the blade 58 of the spreader engages the stop posts 22, as illustrated at the phantom position B of the spreader 16 in FIG. 2. This downward force enables the blade 58 to displace all of the cells from the original location of the sample deposit; also, this initial motion initiates lateral distribution of the blood along the blade 58.

During a brief pause when the spreader 16 is engaged with the post 22, capillary action will spread the blood 13 laterally along the blade 58 so that the clearance space 67 between the slide 14 and the recessed surface 66 of the blade will become substantially filled, as best illustrated in FIG. 4. Thereafter, the spreader 16 is moved forward on the slide in the direction indicated by arrow 42 until it engages the posts 20 in the phantom position C illustrated in FIG. 2. The tapered legs 54 contribute to a smooth movement of the spreader 16 as the legs 54 ride on the slide 14 and the thin, monocellular layer of bloodD illustrated in FIG. 6 is produced as an even trail behind the blade 58 in conformity with a preferred 0.0026 inch dimension of the clearance space 67. The rails 32 and 34 of the base 12 maintain the lateral alignment of the spreader 16 and the slide 14 in both the initial backward movement and the forward movement of the spreader on the slide 14. The bed surface 18 of the base is not subjected to the concentrated downward pressure imposed by the legs 54 because they engage only the slide 14 and thereby prevent grooving or deformation thereat.

Minor variations in the size and structural features of cooperating parts and in materials used may occur to the skilled artisan without departing from the crux of the invention, the scope of which is set forth in the claims hereto appended.

I claim:

1. Apparatus for preparing a monolayer film of a biological fluid sample, such as blood or the like, on a slide for microscopic analysis, comprising:
    A. a base having opposite extremities and a flat upper surface between said extremities for supporting a slide thereon and a pair of upstanding guide rails extending along opposite side edges of the surface;
    B. a spreader for linear movement between said extremities relative to and engaged with the slide for spreading the sample into a monolayer on the slide comprising:
        i. a generally planar platform having first and second ends,
        i.i. a pair of spaced apart leg members depending from the platform adjacent said first end,
        i.i.i. a sample spreading blade member depending from the platform adjacent said second end; and
        i.v. means for moving said spreader linearly,
    C. said spreader being constructed and arranged to be positioned for such movement between the guide rails with both said leg members and blade riding on the slide so that when a sample has been deposited on the slide resting on the said surface, said spreader is movable linearly to enable the blade member to form said monolayer during such linear movement of the spreader between said extremities without engaging said surface.

2. The apparatus as claimed in claim 1 wherein said base includes rigidifying means depending from said surface to prevent deformation of said surface under downward force exerted upon said spreader during said movement.

3. The apparatus as claimed in claim 2 wherein said rigidifying means comprise at least one rib member depending from said surface.

4. The apparatus as claimed in claim 2 wherein said rigidifying means comprise a plurality of spaced apart rib members extending across a substantial part of the length of said base.

5. The apparatus as claimed in claim 1 wherein said guide rails are spaced apart selectively relative to the width of the spreader so as to maintain desired alignment of the spreader and the slide.

6. The apparatus as claimed in claim 1 wherein each of said leg members is tapered at the bottom end thereof whereby to reduce the area of engagement thereof with the slide during such linear movement.

7. The apparatus as claimed in claim 1 wherein said means for moving said spreader comprise a pair of projections upstanding from said platform for manually gripping said spreader.

* * * * *